United States Patent [19]

Schoolnik et al.

[11] Patent Number: 5,415,995
[45] Date of Patent: May 16, 1995

[54] DIAGNOSTIC PEPTIDES OF HUMAN PAPILLOMA VIRUS

[75] Inventors: Gary K. Schoolnik, Palo Alto; Joel M. Palefsky, Redwood City, both of Calif.

[73] Assignee: The Board of Trustees of the Leland Stanford Junior University, Palo Alto, Calif.

[21] Appl. No.: 909,122

[22] Filed: Jul. 6, 1992

Related U.S. Application Data

[60] Continuation of Ser. No. 221,276, Jul. 19, 1988, abandoned, which is a division of Ser. No. 884,184, Jul. 10, 1986, Pat. No. 4,777,239.

[51] Int. Cl.⁶ ............................................. G01N 33/53
[52] U.S. Cl. ................................. 435/7.1; 435/7.36; 435/236; 514/12; 530/324; 530/326; 530/327; 530/328
[58] Field of Search ............... 435/6, 7.1, 7.36, 236; 935/32; 514/12; 530/324, 326–328, 387

[56] References Cited

U.S. PATENT DOCUMENTS

| | | | |
|---|---|---|---|
| 4,079,127 | 3/1978 | Goldstein et al. | 424/177 |
| 4,419,446 | 12/1983 | Howley et al. | 435/68 |
| 4,554,101 | 11/1985 | Hopp | 260/112.5 |
| 4,609,548 | 9/1986 | Kit et al. | 424/89 |
| 4,686,186 | 8/1987 | Sugden | 435/243 |
| 4,777,239 | 10/1988 | Schoolnic et al. | 530/326 |

FOREIGN PATENT DOCUMENTS 0044710 7/1981 European Pat. Off. .
8605816 10/1986 WIPO .

OTHER PUBLICATIONS

Smotkin et al. *Proc. Natl. Acad. Sci. USA*, vol. 83, Jul. 1986, "Transcription of Human Papillomavirus Type 16 early Genes in a Cervical Cancer and a Cancer-Derived Cell Line and Identification of the E7 Protein", pp. 4680–4684.
Seedorf et al. *Virology*, 145, 1985, "Human Papillomavirus Type 16 DNA Sequence", 181–185.
Hopp et al., Proc. Natl. Acad. Sci. USA, vol. 78, No. 6, Jun. 1981, Prediction of Protein Antigenic Determinants from A. A. Sequences, pp. 3824–3828.
Burk, et al, *J. Cell. Biochem. Supplement 9C*, "Papilloma Viruses: Molecular and Clinical Aspects", Abstract 1312, p. 69, 1985, Prospective HPV DNA Analysis of Patients with Abnormal Pap Smears.
Rowekamp, et al., *J. Cell. Biochem. Supplement 9C* "Papilloma Viruses: Molecular and Clinical Aspects", Abstract 1364, p. 88, 1985, The Nucleotide Sequence of Human Papilloma Virus Type 16: Expression of Open Reading-Frames in E. coli.
Miesels et al., *Gynecol. Oncol.* (1981) 12:S111–S123.
Crum et al., *Gynecol. Oncol.* (1983) 15:88–94.
Syrjanen et al., *Obstet. Gynecol. Surv.* (1984) 39:252–265.
Baird et al., *Lancet* (1983) 2:17–18.
Zur Hausen et al., *Lancet* (1982) ii:1370–1372.
Ferenczy et al., *Am. J. Surg. Pathol.* (1981) 5:661–670.
Seedorf et al., *Virology* (1985) 145:181–185.
Klug et al., *J. Mol. Biol.* (1965) 11:403–423.
Coggin et al., *Cancer Res.* (1979) 39:545–546.
Yasumoto, *J. Virol.* (1986) 57:572–577.
Tsurokawa et al., *Proc. Natl. Acad. Sci.* (1986) 83:2200–2203.
Tsuchiya et al., *Chem. Abstr.* (1984) 101:673 (abstract No. 73029e).
Danos et al., *Chem. Abstr.* (1983) 99:122 (abstract No. 33750s).

(List continued on next page.)

*Primary Examiner*—Christine M. Nucker
*Assistant Examiner*—Laurie Scheiner
*Attorney, Agent, or Firm*—Cooley Godward Castro Huddleson & Tatum

[57] ABSTRACT

A series of seventeen synthetic peptides which are capable of raising antibodies specific for certain desired human papilloma virus (HPV) are useful in diagnosis and therapy of conditions associated with HPV infection.

2 Claims, 14 Drawing Sheets

OTHER PUBLICATIONS

Staquet et al., *Chem. Abstr.* (1981) 95:474 (abstract No. 148419a).

Smith et al., *Chem. Abstr.* (1981) 94:118 (abstract No. 1141z).

Favre et al., *Chem. Abstr.* (1975) 82:238 (abstract No. 39938a).

Estes et al., *Chem. Abstr.* (1975) 82:227 (abstract No. 82646v).

Levitt et al., *Chem. Abstr.* (1977) 87:188 (abstract No. 147435a).

Orth et al., *Chem. Abstr.* (1977) 87:281 (abstract No. 180411n).

Crawford et al., *Chem. Abstr.* (1973) 78:526 (abstract No. 111744a).

Rolstad et al., *Biol. Abstr.* (1985) 79(12) (abstract No. 104971).

Mueller et al., *Biol. Abstr.* (1980) 69(1):723–724 (abstract No. 6847).

Doorbar et al., *EMBO J.* (1986) 5(2):355–362.

```
                    10              20              30
HPV 16  M E T L C Q R L N V  C Q D K I L T H Y E  N D S T D L R D H I
    11  M E A I A K R L D A  C Q D Q L L E L Y E  E N S I D I H K H I
    6B  M E A I A K R L D A  C Q E Q L L E L Y E  E N S T D L H K K V 40              50              60
    16  D Y W K H M R L E C  A I Y Y K A R E M G  F K H I N H Q V V P
    11  M H W K C I R L E S  V L L H K A K Q M G  L S H I G L Q V V P
    6B  L H W K C M R H E S  V L L Y K A K Q M G  L S H I G M Q V V P 70              80              90
    16  T L A V S K N K A L  Q A T E L Q L T L E  T I Y N S Q Y S N E
    11  P L T V S E T K G H  N A I E M Q M H L E  S L A K T Q Y G V E
    6B  P L K V S E A K G H  N A I E M Q M H L E  S L L R T E Y S M E 100             110             120
    16  K W T L Q D V S L E  V Y L T A P T G C I  K K H G Y T V E V Q
    11  P W T L Q D T S Y E  M W L T P P K R C F  K K Q G N T V E V K
    6B  P W T L Q E T S Y E  M W Q T P P K R C F  K K R G K T V E V K 130             140             150
    16  F D G K I C N T M H  Y T N W T H I Y I C  E E A S V T V V E G
    11  F D G C E D N V M E  Y V V W T H I Y L Q  D N D S W V K V T S
    6B  F D G C A N N T M D  Y V V W T D V Y V Q  D N D T W V K V H S 160             170             180
    16  Q V D Y Y G L Y Y V  H E G I R T Y F V Q  F K D D A E K Y S K
    11  S V D A K G I Y Y T  C G Q F K T Y Y V N  F N K E A Q K Y G S
    6B  M V D A K G I Y Y T  C G Q F K T Y Y V N  F V K E A E K Y G S 190             200             210
    16  N K V W E V H A G G  Q V L C P T S V F   S S N E V S S P E I
    11  T N H W E V C Y G S  T V I C S P A S V S  S T V R E V S I A E P
    6B  T K H W E V C Y G S  T V I C S P A S V S  S T T Q E V S I P E S
```

FIG. 2-1

```
                           220                     230                       240
16   I R Q H L A N H P A   A T H T K A V A L G   T E E T Q T T I Q R
11   T T Y T P A Q T T A   P T       V S A C T   T E D G V S S P P R
6B   T T Y T P A Q T S T   L         V S S S T   K E D A V Q T P P R 250                     260                       270
16   P R E S P D T G N P   C H T K L L H R D     S V D S A P I L T A
11   K R ARS P S T N N       T L C V A N I R     S V D S TINN I V T D
6B   K R ARS V Q Q S P     C N A L C V A H I G   P V D S GNHN L I T N 280                     290                       300
16   F N S S H K G R I N   C N S N T T P I V H   L K G D A N T L K C
11   N Y N K H Q R R N N   C H S A A T P I V Q   L Q G D S N C L K C
6B   N H D Q H Q R R N N   S N S S A T P I V Q   F Q G E S N C L K C 310                     320                       330
16   L R Y R F K K H C T   L Y T A V S S T W H   W T G H N V K H K S
11   F R Y R LND K Y K H   L F E L A S S T W H   W A S P E A P H K N
6B   F R Y R LND R H R H   L F D L I S S T W H   W A S S K A P H K H 340                     350                       360
16   A I V T L T Y D S E   V Q R D Q F L S Q V   K T P K T I T V S T
11   A I V T L T Y S S E   E Q R Q Q F L N S V   K I P P T I R H K V
6B   A I V T V T Y D S E   E Q R Q Q F L D V V   K I P P T I S H K L

```
                    10              20                30
HPV 16  M H Q K R T A M F Q  D P Q E R P R K L P  Q L C T E L Q T T I
    18  M         A R F E  D P T R R P Y K L P  D L C T E L S T S L
    11  M E S K DASTS A T S I  D                 Q L C K T F N L S L
    68  M E S A NASTS A T T I  D                 Q L C K T F N L S M 40              50                60
    16  H D I I L E C V Y C  K Q Q L L R R E V Y  D F A F R D L C I V
    18  Q D I E I T C V Y C  K T V L E L T E V F  E F A F K D L F-V V
    11  H T L Q I Q C V F C  R N A L T T A E I Y  A Y A Y K N L K V V
    68  H T L Q I N C V F C  K N A L T T A E I Y  S Y A Y K H L K V L 70              80                90
    16  Y R D G N P Y A V C  D K C L K F Y S K I  S E Y R H Y C Y S L
    18  Y R D S I P H A A C  H K C I D F Y S R I  R E L R H Y S D S V
    11  W R D N F P F A   C  A C L E L Q G K I    N Q Y R H F N Y A A
    68  F R K K Y P Y A A C  A C L E F H G L I    N Q Y R H F D Y A K 100             110               120
    16  Y G T T L E Q Q Y N  K P L C D L L I R C  I N C Q K P L C P E
    18  Y G D T L E K L T N  T G L Y N L L I R C  L R C Q K P L N P A
    11  T A P T V E E E T N  E D I L K V L I R C  Y L C H K P L C E I
    68  Y A T T V E E E T K  Q D I L D V L I R C  Y L C H K P L C E V 130             140               150
    16  E K Q R H L D K K Q  R F H N I R G R W T  G R C M S C C R S S
    18  E K L R H L N E K R  R F H N I A G H Y R  G Q C H S C CNRR R Q E
    11  E K L K H I F R K A  R F I K L N N Q W K  G R C L H C W T T C
    68  E K V K H I L T K A  R F I K L N C T W K  G R C L H C W T T C

```
HPV                    10                    20                         30
 16   MHGDTPTLHE YMLDLQPETT DLYCYEQLND
 11   MHGRLVTLKD IVLDLQPPDPV GLHCYEQLED
 6B   MHGRHVTLKD IVLDLQPPDPV GLHCYEQLVD 40                    50                         60
 16   SSEEDEIDG  PAGQAEPDRA HYNIVTFCCK
 11   SSL EDEVDK VDKQDAQPLTQ HYQILTCCCG
 6B   SSEDEVDEVD GQDS QPLKQ HFQIVTCCCG 70                    80                         90
 16   CDSTLRLCVQ STHVDIRTLE DLLMGTLGIV
 11   CDSNVRLVVE CTDGDIRQLQ DLLLGTLNIV
 6B   CDSNVRLVVQ CTETDIREVQ QLLLGTLNIV

16   CPICSQKP   98
 11   CPICAPKP   98
 6B   CPICAPKT   98
```

FIG. 4

```
                  10                    20                      30
HPV 16   M Q V T F I Y I L V   I T C Y E N D V N V   Y H I F F Q M S L W
    11                                                             M W
    6B                                                             M W 40                    50                      60
    16   L P S E A T V Y L P   P V P V S K V V S T   D E Y V A R T N I Y
    11   R P S D S T V Y VpP   P N P V S K V V A R   M R M L N A P T Y F
    6B   R P S D S T V Y VpP   P N P L S K V V A T   D A Y V T R T N I F 70                    80                      90
    16   Y H A G T S R L L A   V G H P Y F R I K K   P N N N K I L V P K
    11   I M P ? S S R L L A   V G H P Y Y S I K K     V N K T V V P K
    6B   Y H A S S S R L L A   V G H P Y F S I K R     A N K T V V P K 100                   110                     120
    16   V S G L Q Y R V F R   I H L P D P N K F G   F P D T S F Y N P D
    11   V S G Y Q Y R V F K   V V L P D P N K F A   L P D S S L F D P T
    6B   V S G Y Q Y R V F K   V V L P D P N K F A   L P D S S L F D P T 130                   140                     150
    16   T Q R L V W A C V G   V E V G R G Q P L G   V G I S G H P L L N
    11   T Q R L V W A C T G   L E V G R G Q P L G   V G V S G H P L L N
    6B   T Q R L V W A C T G   L E V G R R Q P L G   V G V S G H P F L N 160                   170                     180
    16   K L D D T E N A S A   Y A A N A G V D N R   E C I S M D Y K Q T
    11   K Y D D V E N S G G   Y G G N P G Q D N R   V N ? G M D Y K Q T
    6B   K Y D D V E N S   G   S G G N P G Q D N R   V N V G M D Y K Q T 190                   200                     210
    16   Q L C L I G C K P P   I G E H W G K G S P   C T N V A V N P G D
    11   Q L C M V G C A P P   L G E H W G K G T Q   C S N T S V Q N G D
    6B   Q L C M V G C A P P   L G E H W G K G K Q   C T N T P V Q A G D
```

FIG. 5-I

```
                        220                    230                    240
HPV 16   C P P L E L I N T V    I Q D G D M V H T G    F G A M D F T T L Q
    11   G P P L E L I T S V    I Q D G D M V D T G    F G A M N F A D L Q
    68   G P P L E L I T S V    I Q D G D M V D T G    F G A M N F A D L Q 250                    260                    270
    16   A N K S E V P L D I    C T S I C K Y P D Y    I K M V S E P Y G D
    11   T N K S D V P L D I    C G T V C K Y P D Y    L Q M A A D P Y G D
    68   T N K S D V P I D I    C G T T C K Y P D Y    L Q M A A D P Y G D 280                    290                    300
    16   S L F F Y L R R E Q    M F V R H L F N R A    G T V G E N V P D D
    11   R L F F Y L R K E Q    M F A R H F F N R A    G T V G E P V P D D
    68   R L F F F L R K E Q    M F A R H F F N R A    G E V G E P V P D T 310                    320                    330
    16   L Y I K G S G S T A    N L A S S N Y F P T    P S G S M V T S D A
    11   L L V K G G N N R S    S V A S S I Y V H T    P S G S L V S S E A
    68   L I I K G S G N R T    S V G S S I Y V N T    P S G S L V S S E A 340                    350                    360
    16   Q I F N K P Y W L Q    R A Q G H N N G I C    W G N Q L F V T V V
    11   Q L F N K P Y W L Q    K A Q G H N N G I C    W G N H L F V T V V
    68   Q L F N K P Y W L Q    K A Q G H N N G I C    W G N Q L F V T V V 370                    380                    390
    16   D T T R S T N M S L    C A A I S T S E T T    Y K N T N F K E Y L
    11   D T T R S T N M T L    C A S V S K S A T     Y T N S D Y K E Y M
    68   D T T R S T N M T L    C A S V T T S S T     Y T N S D Y K E Y M 400                    410                    420
    16   R H G E E Y D L Q F    I F Q L C K I T L T    A D V M T Y I H S M
    11   R H V E E F D L Q F    I F Q L C S I T L S    A E V M A Y I H T M
    68   R H V E E Y D L Q F    I F Q L C S I T L S    A E V M A Y I H T M
```

| HPV | 430 | | | 440 | | | 450 | |
|---|---|---|---|---|---|---|---|---|
| 16 | N S T I | L E D W N F | G L Q | P P P | G T L | E D T Y R F | V T Q | A |
| 11 | N P S V | L E D C N F | G L S | P P P | N G T L | E D T Y R Y | V gs Q | A |
| 68 | N P S V | L E D W N F | G L S | P P P | N G T H | E D T Y R Y | V gs Q | A |

| HPV | 460 | | 470 | | 480 | |
|---|---|---|---|---|---|---|
| 16 | I A C Q K | H T P P A | P K E D D P | L K K Y | T F W E V N L K E K | |
| 11 | I T C Q K | P T P E K | E K Q D P Y K D M | | S F W E V N L K E K | |
| 68 | I T C Q K | P T P E K | E K P D P Y K N L | | S F W E V N L K E K | |

| HPV | 490 | | 500 | | 510 | |
|---|---|---|---|---|---|---|
| 16 | F S A D L D Q | F P L | G R K F L L Q | A G L | K A K P K F | T L G K |
| 11 | F S A D L D Q | F P L | G R K F L L Q | S G Y | R G R T S AR | T G I K |
| 68 | F S A D L D Q | Y P L | G R K F L L Q | S G Y | S G R T S IR | T G V K |

| HPV | 520 | | 530 | | |
|---|---|---|---|---|---|
| 16 | R K A T P T T | S S T | S T T A K R K K R K | L | 531 |
| 11 | R | P A V S K P | S T A P K R K R T K | T K K | 501 |
| 68 | R | P A V S K A | S A A P K R K R A K | T K P | 500 |

```
              10                    20                     30
HPV 16  M R H K R S A K R T   K R A S A T Q L Y K   T C K Q A G T C P P
    11  M K P   R   A R R R   K R A S A T Q L Y Q   T C K A T G T C P P
    6B  M A H S R   A R R R   K R A S A T Q L Y Q   T C K L T G T C P P 40                    50                     60
    16  D   I P K V E G K T   I A E Q I L Q Y G S   M G V F F G G L G I
    11  D V I P K V E H T T   I A D Q I L K W G S   L G V F F G G L G I
    6B  D V I P K V E H N T   I A D Q I L K W G S   L G V F F G G L G I 70                    80                     90
    16  G T G S G T G G R T   G Y I P L G T R P P   T A T D T L A P V R
    11  G T G A G S G G P A   G Y I P L G S S P K   P A I T G G P A A R
    6B  G T G S A T R G R T   G Y V P L Q T S A K   P S I T S G P M A R 100                   110                    120
    16  P P L T V D P V G P   S D P S I V S L V E   E T S F I D A G A P
    11  P P V L V E P V A P   S D P S I V S L I E   E S A I N A G A P
    6B  P P V V V E P V A P   S D P S I V S L I E   E S A I N A G A P 130                   140                    150
    16  T S V P S I P P D V   S G F S I T T S T D   T T P A I L D I N N
    11  E V V     P P T Q     G G F T I T S S E S   T T P A I L D V S V
    6B  E I V     P P A H     G G F T I T S S E T   T T P A I L D V S V 160                   170                    180
    16  T V T T V T T H N N   P T F T D P S V L Q   P P T P A E T G G H
    11  T N H T T T S V F Q N P L F T E P S V I Q   P Q P P V E A S G H
    6B  T S H T T T S I F R N P V F T E P S V T Q   P Q P P V E A N G H 190                   200                    210
    16  F T L S S S T I S T   H N Y E E I P M D T   F I V S T N P N T V
    11  I L I S A P T I T S   Q H V E D I P L D T   F V V S S S D S G P
    6B  I L I S A P T V T S   H P I E E I P L D T   F V V S S S D S G P
```

FIG. 6-1

```
                          220                    230                      240
HPV 16    T S S T P I P G S R    P V A R L G L Y S R    T T Q Q V K V V D P
    11    T S S T P L P R A F    P R P R V G L Y S R    A L Q Q V Q V T D P
    68    T S S T P V P G T A    P R P R V G L Y S R    A L H Q V Q V T D P 250                    260                      270
    16    A F V T P T K L I      T Y D N P A Y E G I    D V D N T L Y F S S
    11    A F L S T P Q R L V    T Y D N P V Y E G E    D V     S L Q F T
    68    A F L S T P Q R L I    T Y D N P V Y E G E    D V     S V Q F S 280                    290                      300
    16    N D N S I N I A P D    P D F L D I V A L H    R P A L T S R R T G
    11      H E S I H N A P D    E A F M D I I R L H    R P A I T S R R G L
    68      H D S I H N A P D    E A F M D I I R L H    R P A I A S R R G L 310                    320                      330
    16    I R Y S R I G N K Q    T L R T R S G K S I    G A K V H Y Y D L
    11    V R F S R I G Q R G    S ? ? ? ? ? ? ? ?     ? ? ? ? ? ? ? ? ?
    68    V R Y T R I G Q R G    S M H T R S G K H I    G A R I H Y F Y D I 340                    350                      360
    16    S T I D P A E E I E    L Q T I T P S T Y T    T T S H A A S P T S
    11    ? ? ? ? ? ? A E E ? E  L H P L V A A E N D    T F D I Y A   E P
    68    S P I AQA A E E I E    M H P L V A A Q D D    T F D I Y A   E S 370                    380                      390
    16    I N N G L Y D I Y A    D D F I T D T S T T    P V P S V P S T S L
    11    F D P I   P D P V      Q H S V T     Q S      Y L T S T P N T
    68    F E P G   I N P T      Q H P V T N I S D T    Y L T S T P N T 400                    410                      420
    16    S G I Y P A N T T I    P F G G A Y N I P L    V S G P D I P I N I
    11    L S Q S W G N T T V    P L S I P S D ? F V    Q S G P D I T F P T
    68    V T Q P W G N T T V    P L S L P N D L F L    Q S R P D I T F P T
```

FIG. 6-2

```
            430            440              450
HPV 16  TDQAPSLI P I  VPGS P QYTII  ADAG D FYLHP      473
     11  ASMGTPFS P V  TPAL P TGPVF  ITGS D FYLHP     455
     68  APMGTPFS P V  TPAL P TGPVF  ITGS G FYLHP     459

460            470
     16  SY Y ML R KRRK  R L P Y FFSDV S   L A A
     11  TW Y YF A R R RK  R I P L FFSDV    A A
     68  AW Y YF A RKRRK  R I P L FFSDV    A A
```

FIG. 6-3

DIAGNOSTIC PEPTIDES OF HUMAN PAPILLOMA VIRUS

This is a continuation of U.S. Ser. No. 221,276 filed on Jul. 19, 1988, and now abandoned which is in turn a division of U.S. Ser. No. 884,184, filed on Jul. 10, 1986, now issued as U.S. Pat. No. 4,777,239.

TECHNICAL FIELD

The invention relates to vaccines and diagnostics relevant to human papilloma virus (HPV) infection. In particular, synthetic peptides corresponding to regions of putative peptides for types of HPV which infect the genital region raise antibodies useful in diagnosis and in protection against infection.

BACKGROUND ART

Human papilloma virus appears to be associated with the development of cervical carcinoma, a malignant condition which appears to be preceded by several stages of cervical intraepithelial neoplasia (CIN). The association of HPV infection with CIN has long been recognized (Meisels, A., et al, *Gynecol Oncol* (1981) 12:5111–5123; Crum, C. P., et al, ibid (1983) 15:88–94; Syrjanen, K. J., *Obstet Gynecol Surv* (1984) 39:252–265). In fact, IgG reactive with a group-specific papilloma virus antigen was detected in 93% of women with cervical carcinoma and 60% of those with CIN, but not in any control subjects (Baird, P. J., *Lancet* (1983) 2:17–18), and the presence of HPV DNA in these lesions has been recognized by several groups.

There are approximately forty different types of HPV, which are classified by DNA sequence homology using hybridization techniques. Samples having more than 50% homology, as judged by hybridization, are placed into the same type designation. The various types appear to be rather tissue specific. HPV-6, HPV-11, HPV-16, HPV-18, and HPV-31 appear to be associated with the genital tract; others appear to be associated with warts or epidermal dysplasias in other tissues. However, HPV-6 and HPV-11 are associated with condyloma type lesions, while HPV-16, HPV-18 and HPV-31 are associated with cervical intraepithelial neoplasia, including invasive carcinoma.

The relationship of HPV infection to the development of CIN and cervical carcinoma is unclear, however it has been postulated that HPV acts as an initiator in cervical carcinogenesis and that malignant transformation depends on interaction with other factors (Zur Hausen, H., et al, *Lancet* (1982) ii:1370). The incidence of HPV infection appears to be increasing as shown by a 700% increase in patient visits related to genital HPV infections in both males and females between 1966 and 1981 (Center for Disease Control: Nonreported Sexually Transmitted Diseases (1979) MMWR 28:61) and the presence of HPV in more than 3% of pap smears of women under 30 (Ferenczy, A.. et al, *Am J Surg Pathol* (1981) 5:661–670).

The nature of HPV-16 in particular, and papilloma viruses in general has been well studied recently. HPV-16 is a member of the Papova virus group and contains a 7904 bp double-stranded DNA genome (Siedorf, K., et al, *Virology* (1985) 145:181–185). The capsid is 50 nm and contains 72 capsomers (Klug, A., *J Mol Biol* (1965) 11:403–423). There are a number of subtypes of HPV-16 which are isolates showing greater than 50% homology (Coggin, *Cancer Research* (1979) 39:545–546), but differences in restriction in endonuclease patterns.

The DNAs of several papilloma viruses have been sequenced, including several HPV types, bovine papilloma virus (BPV) and cottontail rabbit papilloma virus (CRPV). All of these display similar patterns of nucleotide sequence with respect to open reading frames. The open reading frames can be functionally divided into early region (E) and late regions (L); the E region is postulated to encode proteins needed for replication and transformation: and L region to encode the vital capsid proteins (Danos, O., et al, *J Invest Derm* (1984) 83:7s–11s).

The detection of HPV in cervical samples has been difficult because there is no tissue culture system capable of supporting virus harvested from the tissue to be tested through its replication cycle (Tichman, et al, *J Invest Derm* (1984) 83:25–65). There is, however, a recently reported in vitro transformation assay (Yasumoto, S. *J Virol* (1986) 57: 572–577), Tsurokawa, U. et al *Proc Nat'l Acad Sci* (USA) (1986) 83: 2200–2203. It is believed that because of analogy with the better studied BPV and CRPV systems, the proteins encoded by several early open reading frames, for example, E6, E5, E7 and E2 (see FIG. 1) are important in HPV genital infections. However, no system for utilization of peptides associated with these regions has been suggested either as an aid to diagnosis or in the synthesis of a vaccine.

DISCLOSURE OF THE INVENTION

The present invention provides peptides selected on the basis of predicted secondary structure and hydrophilicity from proteins or peptides encoded by selected open reading frames. The secondary structure and hydrophilicity are deduced from the amino acid sequence of these proteins according to methods disclosed by Hopp, T., et al, *Proc Natl Acad Sci (USA)* (1981) 78:3824; Levitt, M., *J Mol Biol* (1976) 104:59; and Chou, P., et al, Biochem (1974) 13:211. The results of these deductions permit the construction of peptides which elicit antibodies reactive with the entire protein, as is further described below. Two general types of such antigenic peptides are prepared. Peptide regions identified as being specific to HPV-16 or other HPV type-specific determinants by lack of homology with other HPV types lead to the peptides which are useful to raise antibodies for diagnostic, protective, and therapeutic purposes against HPV-16 or other virus type per se. Peptide regions which are homologous among the various types of HPV of interest are useful as broad spectrum diagnostics and vaccines, and elicit antibodies that are broad spectrum diagnostics.

Accordingly, in one aspect, the invention is directed to peptides of the following sequences deduced from the noted regions of HPV-16:

(1) Ser-Arg-Ser-Ser-Arg-Thr-Arg-Arg-Glu-Thr-Gln-Leu (SEQ ID NO:1) (representing residues 147–158 of E6 except Ser was substituted for Cys at position 1):

(2) Phe-Gln-Asp-Pro-Gln-Glu-Arg-Pro-Arg-Lys-Leu- Pro-Gln-Leu-Cys (SEQ ID NO:2), representing residues 9–23 of E6;

(3) Thr-Glu-Leu-Gln-Thr-Thr-Ile-His-Asp-Ile-Ile-Leu-Glu-Cys (SEQ ID NO:3), representing residues 24–37 of E6;

(4) Leu-Arg-Arg-Glu-Val-Tyr-Asp-Phe-Ala-Phe-Arg-Asp-Leu-Cys (SEQ ID NO:4), representing residues 45-58 of E6;

(5) Asp-Lys-Lys-Gln-Arg-Phe-His-Asn-Ile-Arg (SEQ ID NO:5), representing residues 127-136;

(6) Gly-Pro-Ala-Gly-Gln-Ala-Glu-Pro-Asp-Arg-Ala (SEQ ID NO:6), representing residues 40-50 of E7;

(7) Asp-Thr-Pro-Thr-Leu-His-Glu-Tyr-Met (SEQ ID NO:7), representing residues 4-12 of E7;

(8) Asn-Asp-Ser-Ser-Glu-Glu-Glu-Asp-Glu-Ile-Asp-Gly (SEQ ID NO:8), representing residues 29-40 of E7;

(9) Leu-Gln-Leu-Thr-Leu-Glu-Thr-Ile-Tyr-Asn-Ser (SEQ ID NO:9), representing residues 75-85 of E2;

(10) Ile-Ile-Arg-Gln-His-Leu-Ala-Asn-His-Pro (SEQ ID NO:10), representing residues 210-219 of E2;

(11) His-Pro-Ala-Ala-Thr-His-Thr-Lys-Ala-Val-Ala-Leu-Gly (SEQ ID NO:11), representing residues 218-230 of E2;

(12) Ser-Glu-Trp-Gln-Arg-Asp-Gln-Phe-Leu-Ser-Gln-Val (SEQ ID NO:12), representing residues 339-350 of E2;

(13) Asp-Gln-Asp-Gln-Ser-Gln-Thr-Pro-Glu-Thr-Pro (SEQ ID NO:13), representing residues 48-58 of E4;

(14) Gly-Ser-Thr-Trp-Pro-Thr-Thr-Pro-Pro-Arg-Pro-Ile-Pro-Lys-Pro (SEQ ID NO:14), representing amino acids 20-34 of E4;

(15) Arg-Leu-Tyr-Leu-His-Glu-Asp-Glu-Asp-Lys-Glu-Asn (SEQ ID NO:15), representing amino acids 476-487 of E1; and

(16) Ala-Pro-Ile-Leu-Thr-Ala-Phe-Asn-Ser-Ser-His-Lys-Gly-Cys (SEQ ID NO:16), representing amino acids 218-230 of E2;

wherein all the foregoing are derived from Type 16; and

(17) Glu-Ser-Ala-Asn-Ala-Ser-Thr-Ser-Ala-Thr-Thr-Ile-Cys (SEQ ID NO:17), representing amino acids 6-17 of the E6 reading frame of Type 6B.

Each of the foregoing peptides, designated herein peptide 1, peptide 2, etc, i.e. peptides 1-17, may, if it does not already have this residue, be prepared with an additional C-terminal cysteine for ease in conjugation to a neutral carrier, and in another aspect, the invention relates to peptides containing this additional cysteine.

In addition, the invention relates to a method for synthesizing peptides useful in the various aspects of the invention, which method comprises preparing an analysis of the secondary structure and hydrophilicity of peptides encoded by the open reading frames of the DNA corresponding to HPV vital types associated with genital infection, and selecting regions of secondary structure corresponding to areas on the surface capable of eliciting antibodies reactive with the entire protein. The selected peptide regions are then prepared synthetically using either solid phase synthesis or other suitable techniques. The invention also relates to peptides prepared using this method. The peptides thus prepared can be designed as specific to a particular virus type or may be capable of raising antibodies cross-reacting against the range of HPV associated with genital infection depending on the use desired. Like the specific peptides numbered 1-17 above, these may also be prepared with a C-terminal cysteine for ease in conjugation.

In further aspects, the invention relates to the foregoing peptides conjugated to carriers capable of conferring immunogenicity on these peptides, to antisera raised against these peptides and the antibodies contained in these sera, to methods of diagnosing the presence of HPV in tissue utilizing these antisera, to methods of detecting anti-HPV antibodies using the peptides per se, and to kits useful in such assays.

BRIEF DESCRIPTION OF THE DRAWINGS

FIG. 2 shows comparison of the amino acid sequences in the E2 open reading frame for various human papilloma viruses.

FIG. 3 shows comparison of the amino acid sequences in the E6 open reading frame for various human papilloma viruses.

FIG. 4 shows comparison of the amino acid sequences in the E7 open reading frame for various human papilloma viruses.

FIG. 5 shows comparison of the amino acid sequences in the L1 open reading frame for various human papilloma viruses.

FIG. 6 shows comparison of the amino acid sequences in the L2 open reading frame for various human papilloma viruses.

FIG. 8 shows the staining of a cervical biopsy at stage CIN2 using immunoperoxidase staining mediated by the antibodies of the invention:

MODES OF CARRYING OUT THE INVENTION

Figure 1:
FIG. 1 shows the distribution of open reading frames in various papilloma viruses.

The peptides of the invention are used to raise antibodies, either in subjects for which protection against infection by HPV is desired, i.e. as vaccines or to heighten the immune response to an HPV infection already present. They are also injected into production species to obtain antisera useful in diagnosis. In lieu of the polyclonal antisera obtained in the production subjects, monoclonal antibodies may be produced using the method of Kohler and Milstein or by more recent modifications thereof by immortalizing spleen or other antibody-producing cells from injected animals to obtain antibody-producing clones.

In any event, the polyclonal or monoclonal antibodies obtained are useful for diagnosis of HPV infection in cervical biopsies or pap smears and in assessing disease levels in human or other subjects. In particular, diagnosis using the antibodies of the invention permits identification of patients at high risk for malignant transformation as well as identification of the particular phase of CIN associated with the sample. The antibodies can also be used in analysis of serum to detect the virus or to detect the virus in metastases of infected tissue, as well as to monitor the progress-of therapy with antiviral or other therapeutic agents directed to control of the infection or carcinoma. The antibodies, if corrected for species variations can also be used as passive therapy.

In a converse diagnosis, the peptides of the invention can be used in similar immunoassays to detect the presence of antibodies raised against HPV in the serum of persons suspected of harboring HPV infections or to titrate the sera of persons treated with an anti-HPV vaccine. The use of synthetic peptides for this purpose has the advantage of providing a relatively low cost and reproducible reagent for use in these tests.

Direct administration of the proteins to a host can confer either protective immunity against HPV or, if the subject is already infected, a boost to the subject's own immune response to permit more effective combat of the progress of the disease. For all applications, the peptides are administered in immunogenic form. Since the peptides are relatively short, this necessitates conjugation with an immunogenicity conferring carrier material. This carrier material should ideally be antigenically neutral—i.e., ineffective in raising antibodies against itself. Antigenic neutrality is, of course, an ideal state as many carriers which are actually satisfactory do contain some antigenic regions which are capable of raising antibodies in the host. However, this may still be acceptable if the antigenic regions are in fact different from those of the peptide of interest, which is quite easy to achieve, or if the antibodies raised against the carrier portions are harmless to the subject.

The peptides of the invention are designed for their in vitro synthesis by choosing appropriate regions of the protein encoded by the open reading frames of the HPV types of interest. Regions are chosen for their immunogenic capability and, depending on the use required, for their ability to serve as type specific or broad range vaccines and diagnostics.

Once designed, the peptides of the invention are prepared by any convenient means, commonly by chemical peptide synthesis using solid phase techniques. For conjugation to carrier protein, it is convenient to synthesize these peptides with an additional cysteine residue, for example, at the C-terminus to provide a sulfhydryl group for convenient linkage. Depending on the nature of the linkers used, however, other approaches to form the conjugates are possible. The conjugated peptides are then administered to subject animals.

If the peptides are to be administered as vaccines, they are formulated according to conventional methods for such administration to the subject to be protected. If they are to be used directly, as diagnostic reagents, they are purified and packaged for such use. If they are to be used to produce antibodies for diagnostic purposes, convenient test animals can be used to prepare the appropriate antisera, and these antisera used directly. Suitable hosts include mice, rats, rabbits, guinea pigs, or even larger mammals such as sheep. For administration to such animals, the peptides linked to carrier are generally administered in the presence of an adjuvant, usually Freund's complete adjuvant, and the polyclonal sera are harvested periodically by standard techniques.

If the antibodies are to be used for therapeutic purposes, it is generally desirable to confer species characteristics upon them compatible with the subject to be treated. Accordingly, it is often desirable to prepare these antibodies in monoclonal form since fusion with suitable partners is capable of conferring the desired characteristics on the secreted monoclonals.

These matters are set forth in greater detail below.

Selection of Peptides

At least five HPV types are known to be associated with genital infection, and additional types may be isolated in the future, as it is not certain that all existing types have in fact been detected, and it is expected that mutation will result in appearance of previously nonexistent forms. Of the five types now known, HPV-6 and HPV-11 are associated with benign conditions, while HPV-16, HPV-18 and HPV-31 appear to be associated with malignant transformation. All five of these types, and presumably those still to be found, exhibit similar organization of their DNA, so that all contain, for example, the open reading frames associated with the putative early (E) proteins and late (L) proteins. Depending on the use for which the peptide is intended, appropriate regions of the early or late putative proteins are selected.

The early proteins, as they are thought to be associated with vital replication and transformation, are particularly useful as portions of immunogens administered to production animals to generate antibodies needed for diagnosis of the progress of HPV infection. They are also useful as vaccine components. Reagents associated with the late proteins, as these appear to be associated with capsid proteins, are also useful as vaccines. They are also capable of raising antibodies which are diagnostic for the presence of free virus in the bloodstream and are themselves useful in detecting antibodies raised against the whole virus. Therefore, the first step in the analysis is to ascertain the stage of vital infection which forms the subject matter for the utility.

The second decision point relates to whether the peptide is designed for applications specific to a particular type or a broad spectrum of genital infection-causing HPV. If detection of antigen or antibody associated with a particular type is desired, it is desirable to have a type-specific peptide as the basis for the reagent or antiserum. On the other hand, if a vaccine protective against HPV genital infections in general is desired, or if it is satisfactory to determine the presence or absence of any HPV genital infection, then a peptide associated with a broad spectrum of these virions is desired.

To design species-specific vaccines, regions of the putative proteins encoded by the open reading frames are selected which are not homologous from strain to strain, but characteristic of the particular type of interest. If a broad spectrum peptide is required, reagents of homology are chosen. FIGS. 2–6 show comparisons of amino acid sequences for various open reading frames in several HPV types. These sequences show various regions of homology for these proteins: for example, in the early protein encoding region E2, the region between positions 109–119 is much more homologous than the region between 139 and 148 of the sequence; the region between residues 331 and 350 contains considerable homology, whereas that between positions 241–260 does not.

The third level of selection relates to secondary structure and hydrophilicity. Regions are selected which are considered likely to raise antibodies in the host which are cross-reactive against the entire protein on the basis of the ability of this particular subsection of the protein to mimic its own secondary structure in the native state. Generally, if there is no additional information, one is limited to the use of areas of conformational flexibility such as the N-terminal and C-terminal regions because these regions of the native protein are assumed to exhibit the same spectrum of conformations as the synthesized peptide. A difficulty with this approach, however, is that due to the multiplicity of possibilities, antibody production against a desired conformation may represent a small portion of the antibodies raised and the process is relatively inefficient.

Figure 7:
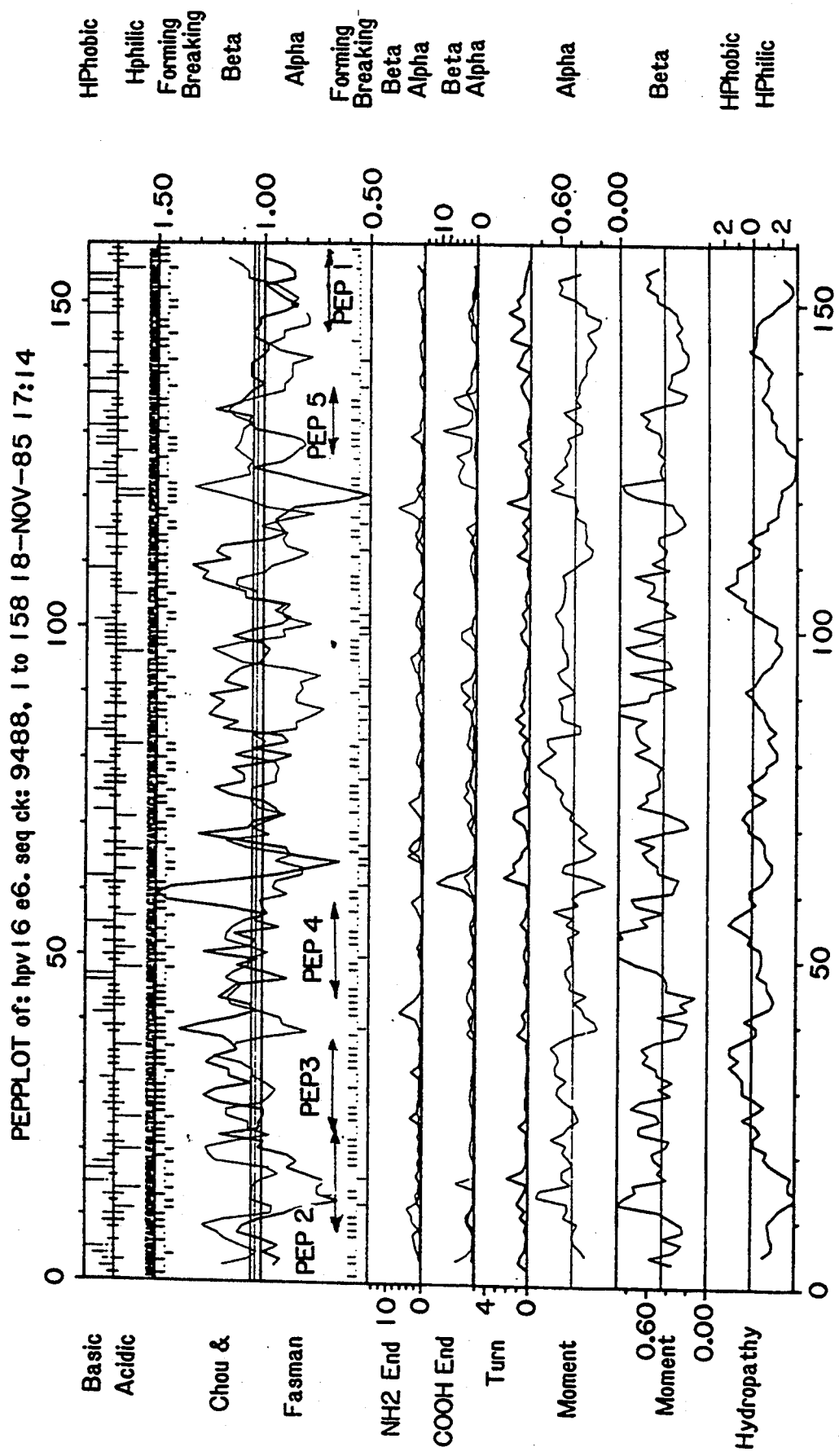
FIG. 7 shows a typical-analysis plot using the referenced methods to ascertain secondary structure in hydrophilicity.

A superior approach is based on ascertaining regions of the protein which are likely to have the same conformation in the intact protein as is exhibited by the synthesized peptide. These are believed to be regions having reversed or beta turns as the formation of these turns is generally associated with the surface of the protein, and is also dependent on the amino acid sequences in close proximity with each other. Methods to ascertain the locations of the desired beta turns are known in the art and described in the paper of Chou and Fassman referenced above. FIG. 7 shows an illustrative plot obtained according to these procedures showing the regions of alpha helixes, beta sheets and reverse turns for the protein encoded by the E7 open reading frame of HPV-16. The results also provide data as to regions of hydrophobicity and hydrophilicity which are significant in the formation of these beta turns. Thus, using FIG. 7 as an illustration, those regions considered likely to exhibit the desired immunogenicity are illustrated as peptides 1–5. In selecting these peptide regions, information is obtained from the plot which shows the presence of beta turns and associated regions of hydrophilicity. This analysis can, of course, be done with respect to the peptides encoded in the open reading frames of any of the desired HPV types.

When the appropriate region is chosen by this analysis, peptides of 8–15 amino acid residues which include this region are synthesized as described below. It is believed that at least 8 amino acids are needed to provide sufficient sequence: peptides longer than 15 amino acids could be synthesized, but at a sacrifice of economy.

Peptide Synthesis

As used herein, "peptide", "polypeptide", and "protein" are used interchangeably, and refer to amino acid sequences of a variety of lengths, either in their neutral (uncharged) forms or in forms which are salts, and either free of modifications such as glycosylation, side chain oxidation, or phosphorylation or containing these modifications. It is well understood in the art that amino acid sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acid side chains, such as glycosyl units, lipids, or inorganic ions such as phosphates, as well as modifications relating to chemical conversions of the chains, such as oxidation of sulfhydryl groups. Thus, "peptide" or its equivalent terms is intended to include the appropriate amino acid sequence referenced, subject to those of the foregoing modifications which do not destroy its immunospecific antigenic properties.

All of the peptides of the invention are sufficiently short that chemical synthesis, using methods now standard in the art, is feasible. A review of such methods is given by, for example, Margolin, A., et al, *Ann Rev Biochem* (1970) 39:841. In most of these procedures, the C-terminal amino acid is bound to a solid support, and reacted with the next amino acid in sequence which has been protected at the amino group to prevent self-condensation. After the initial coupling, the NH$_2$ protecting group is removed, and the coupling process repeated with the amino acid next in order. Polypeptides of considerable chain length have been synthesized in this way. The only requirement is that the amino acid sequence desired to be produced is known.

Recombinant DNA methodology provides an alternative way of synthesizing the desired peptides. The DNA coding sequence for the desired peptide or protein is ligated into an expression vector suitable for transforming a recipient cell, which is thus caused to express the gene and produce the protein. The DNA coding sequences are sufficiently short to be prepared synthetically using means known in the art: see. e.g., Edge, M. P., et al, *Nature* (1981) 292:756.

The coding sequence is placed under the control of control sequences compatible with recombinant hosts in plasmids containing convenient restriction sites for insertion of the desired coding sequence. For example, for bacterial hosts typical of such plasmids are pUC8, and pUC13 available from Messing, J., at the University of Minnesota: (see, e.g., Messing, et al, *Nucleic Acids Res* (1981) 9:309) or pBR322, available from New England Biolabs. Suitable promoters include, for example, the β-lactamase (penicillinase) and lactose (lac) promoter systems (Chang. et al, *Nature* (1977) 198:1056 and the tryptophan (trp) promoter system (Goeddel, D., et al, *Nucleic Acids Res* (1980) 8:4057). The resulting bacterial expression vectors are transformed into suitable bacterial hosts using the calcium chloride method described by Cohen, S. N., et al, *Proc Natl Acad Sci (USA)* (1972) 69:2110, and the transformants selected and cultured. Alternatively, these peptides can be produced in non-bacterial recombinant hosts using appropriate control sequences, vectors and transformation techniques.

Synthesis of Conjugates

Because the peptide sequences of the invention are considered too small to be immunogenic, they are linked to carrier substances in order to confer this property upon them. The carrier substances should be antigenically neutral in the subject generating the antisera.

By "substantially antigenically neutral carrier" is meant a material to which the peptides of the invention may be attached to render them immunogenic, but which does not itself elicit antibodies which will be detrimental to the host, or contain antigenic sites which interfere with the antigenic function of the invention peptides. For example, in subjects which are not beef eaters, such as rabbits or mice, bovine serum albumin (BSA) could be used. For human use, however, carriers are limited to proteins which do not raise antibodies to materials commonly and nonpathogenically encountered by humans. For example, human serum albumin (HSA) or tetanus toxoid protein could be used.

The conjugates can be formed in a variety of ways. For example, there are a large number of heterobifunctional agents which generate a disulfide link at one functional end group and a peptide link at the other, and these have been used extensively. The most popular of these is N-succidimidyl-3-(2-pyridyl dithio) propionate (SPDP). This reagent creates a disulfide linkage between itself and a cysteine residue in one protein and an amide linkage through the amino on a lysine, or other free amino group in the other. A variety of such disulfide/amide forming agents are known. See, for example, *Immun Rev* (1982) 62:185. Other bifunctional coupling agents form a thioether rather than a disulfide linkage. Many of these thioether forming agents are commercially available and include reactive esters of 6- maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. A particularly preferred coupling agent for the method of this invention is succinimidyl 4-(N-maleimido-methyl) cyclohexane-1-carboxylate (SMCC) obtained from Pierce Company, Rockford, Ill.

The foregoing list is not meant to be exhaustive, and modifications of the named compounds can clearly be used. However, if a disulfide or thioether linkage to the peptide is to be employed, and the peptide contains no convenient cysteine, an additional cysteine residue at either terminus can be added when the peptide is prepared. As only shorter peptides require conjugation to carrier, these residues can be included conveniently during chemical synthesis.

Vaccine Preparation

Preparation of vaccines which contain peptide sequences as active ingredients is well understood in the art. Typically, such vaccines are prepared as injectables, either as liquid solutions or suspension: solid forms suitable for solution or suspension in liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgement of the practitioner and are peculiar to each individual. However, suitable dosage ranges for subcutaneous or muscular injection are of the order to 50–500 $\mu$g active ingredient per individual. Suitable regimes for initial administration and booster shots are also variable, but are typified by an initial administration followed in one-two week intervals by a subsequent injection or other administration.

Preparation of Antisera

For preparation of diagnostic antisera, hyperimmune sera can be prepared, for example, in rabbits using standard immunization techniques comprising an initial injection and boosting. The sera can be periodically titrated in a solid phase assay against the immunogenic peptide. For preparation of monoclonal panels, the immunized animals are sacrificed and spleen cells harvested for immortalization to obtain cells capable of producing antibodies. The supernatants of successful immortalized cells are screened for the production of antibodies reactive with the injected peptide. If therapeutic uses are to be made of the monoclonals, the preparation of antisera and immortalization may involve techniques capable of conferring suitable species characteristics on the secreted antibodies. Techniques to obtain antibodies with human characteristics are summarized and disclosed in Teng, N. N. H., at al. in *Human Hybridomas and Monoclonal Antibodies* (1985) Engleman, E., et al. Ed., Plenum Press, p. 71.

Diagnostics

The prepared antisera can be used in a variety of diagnostic assays. All of these are, of course, immunoassays and the design of such assays is of tremendous variety. Perhaps most convenient are solid phase supported immunoassays which employ "sandwiches" in which at least one layer is comprised of the antibodies of the invention and another layer is comprised of sample. In one possible embodiment, the antisera prepared according to the method of the invention are to coat a solid support, such as, for example, a microtiter plate to provide a surface specifically reactive with the HPV components of the sample to be tested. The plates are then treated with sample, and then with an additional antibody also reactive with the desired HPV antigen. The third layer may itself contain a radioactive, fluorescent, or enzymic label or may be reactive with still another layer containing such labels. The variety of protocols for such assays is well understood in the art, and any suitable protocol is acceptable.

With regard to the indications for which the antibodies of the invention are useful in diagnosis, the most commonly encountered use is clearly the diagnosis of the presence or absence of HPV-16 or other relevant HPV either in a pap smear or in cervical biopsy or in biopsies of other tissue. The presence of HPV-16, specifically, and also of HPV-18 or HPV-31, in a cervical biopsy or pap smear is indicative of a high risk for malignant transformation resulting in cervical carcinoma.

The progress of HPV infection to result in the malignant state is believed to pass through three CIN stages, commonly labeled CIN1, CIN2, and CIN3 before finally converting to a malignant transformed carcinoma. The various stages may be associated with expression of different genes of the HPV virus with resulting changes in the level of differentiation of the infected tissue. Therefore, an objective distinction between CIN3 and CIN2 can be made using these antisera, since the differentiated state associated with CIN3 fails to produce a positive response against the antisera raised against the peptides 1–4 of the invention, while that associated with CIN2 does do so. Thus, if the morphological characteristics as to the stage of development of the lesion are unclear, these two stages can be distinguished by virtue of their reactivity with the antisera.

In addition, the antisera are useful in detecting the HPV virus in blood or serum, thus providing a basis for antigen detection in these fluids, or in foreign tissues which would indicate the presence of metastases from an original site. The results of treatment of carcinoma associated with HPV infection can also be followed by assessing the levels of species reactive with these antisera in serum or other tissues. Thus, if the disease is treated, for example, by administration of interferon, the effect of this drug can be monitored by tracking the levels of HPV antigens in serum using the antibodies in this assay.

Conversely, the peptides of the invention can be used in immunoassays to test for the presence or absence of anti-HPV antibodies in serum. The protocol for such assays is similar to that associated with the use of antisera to test for the presence or absence of antigen, except that the sample and reagent are interchanged. These proteins are a convenient source of pure HPV material which thereby permit assays with a minimum of cross reaction.

Therapeutic Uses

The antibodies can also be used therapeutically so long as they are compatible with the host to be treated. Monoclonal preparations having the proper species characteristics are most suitable for this application of the invention which is conducted by injecting into a person already suffering from HPV infection sufficient antibody preparation to combat the progress of the infection.

As noted above, the peptides themselves, in addition to being used as vaccines in advance of infection for protection against the disease, can also be used as an immunomodulation agent when the subject is already infected. By supplying additional immunogenic peptides, the antibody response mounted by the patient is fortified, and is thus more effective in disease control.

Kits

The diagnostic antibodies or peptides of the invention can conveniently be packaged into kits, for the conduct of the immunoassays in which they are the essential reagent. The components of such kits include, typically, the peptide or antibody preparation of the invention, labeled antibody or other protein to permit detection, and optionally, suitable supports and containers for conducting the protocols described. In addition, such kits will contain instructions for utilizing the peptides or antisera of the invention in the context of the samples to be tested and the equipment and reagents provided.

EXAMPLES

The following examples are intended to illustrate but not to limit the invention.

EXAMPLE 1

Preparation of Peptides

Peptides 1–17, further containing a C-terminal cysteine residue are prepared by the solid phase techniques disclosed in Chirgwin, J. M., et al, *Biochem* (1979) 18:5294 using t-Boc protected amino acids and amino acid derivatized polystyrene resin, supplied by Peninsula Laboratories Inc., Belmont, Calif. Asp, Glu, Thr, and Set side chains are protected as O-benzyl esters; Arg and His side chains are protected with tosyl groups; Cys is protected with p-methoxybenzyl; Lys by O-chlorobenzyloxycarbonyl, and Tyr by 2,6-dichloro benzyl. The couplings are performed with 2.5–3 molar excess of t-Boc amino acid and dicyclohexylcarbodiamide (DCC). For couplings of Asn or Gln, a 2.5-fold molar excess of N-hydroxytriazole is also included. Coupling is monitored with ninhydrin and coupling is continued until 99% efficiency is obtained.

After synthesis of the desired chain, protecting groups and resin are cleaved simultaneously by anhydrous hydrogen fluoride in the presence of dimethyl sulfoxide and anisol. The cleaved peptide is extracted with ether, isolated from the resin by extraction with 5% acetic acid, and lyophilized several times. The purity of the final product is determined by reverse phase HPLC on Licosorb RP18 (Merck Dormstät FRG) and by amino acid analysis.

EXAMPLE 2

Conjugation to Carrier Protein

Each of the peptides 1–17, synthesized in Example 1 is conjugated to thyroglobin or to bovine serum albumin. In either case. 10 mg of the carrier protein are dissolved in 3 ml PBS. pH 7.4. and mixed with 1 ml distilled DMF containing 5 mg of the cross-linker m-malenimidobenzoyl-N-hydroxysuccinimidyl ester (MBS) for thyroglobin and succinimidyl 4-(N-malenimido methyl)cyclohexane-1-carboylate (SMCC) for bovine serum albumin.

In the meantime, each of the peptides 1–17 is reduced with sodium borohydride for 15 min on ice to ensure the presence of a free sulfhydryl. After destroying excess borohydride with HCl, the neutralized and reduced peptide is combined with the carrier cross-linker conjugate and stirred overnight at room temperature. The resulting peptide carrier conjugate is isolated by gel filtration on Sephadex G25 in 0.1M ammonium bicarbonate buffer, pH 7.5. and the molar ratio of peptides to carrier determined in the product.

EXAMPLE 3

Preparation of Antisera

Hyperimmune sera are prepared in female New Zealand white rabbits using the conjugates prepared in Example 2. Two rabbits are immunized for each of the peptides 1–17 carrier conjugates. Five hundred μg of thyroglobin-MBS-peptide conjugate are emulsified in Freund's adjuvant and injected subcutaneously and intramuscularly at multiple cites. The rabbits are boosted at six weeks with the same immunogen emulsified with incomplete Freund's adjuvant, and one week later the animals are bled by cardiac puncture. The animals are boosted one week later, bled two weeks later, boosted a third time three weeks later and bled a third time four weeks after the initial cardiac puncture. The antisera are then evaluated in the microtiter solid phase binding assay using peptide-SMCC-BSA conjugate as antigen.

EXAMPLE 4

Titration of Antisera

Wells of disposable polystyrene U microtiter plates are coated with peptide-BSA conjugate in 0.1M sodium carbonate buffer, pH 9.6 for 12 hr at room temperature. The wells are then washed three times with NaCl-brij. Serially diluted antisera are added in PBS-brij-BSA and incubated at 37° C. for 2 hr and washed. Approximately 20,000 cpm of $^{125}$I-protein A in PBS-BSA-brig is added to each well and incubated at 37° C. for 1 hr and washed. The wells are assayed for radioactivity in a gamma scintillation counter, negative controls are non-sensitized wells, wells which are not exposed to antisera and wells exposed to preimmune sera. Each sample is performed in triplicate and recorded as the mean.

EXAMPLE 5

Use of Antisera in Immunoassays

Four of the antisera prepared in Example 4 are used to assess cervical swabs and biopsies for the presence of HPV virus in correlation to various CIN stages and malignant cervical carcinoma. Samples are obtained from patients referred to dysplasia clinics for history of abnormal pap smears. Cervical biopsy material is frozen and stored.

To conduct the assays, several protocols may be employed, including immunoperoxidase staining of pap smears and cervical biopsies, dot immunobinding of cervical smears, Western blot, and immunoprecipitation.

For cervical swabs immunobinding on nitrocellulose paper is conveniently employed. Cervical swabs are spotted onto a 1 cm$^2$ section of nitrocellulose paper, pore size 0.2 μm as described by Jahn, et al, *Proc Natl Acad Sci (USA)* (1984) 81:1684–1687. The paper is air dried and fixed for 15 min in a 10% v/v acetic acid, 25% v/v isoproponyl solution, rinsed, preincubated for 5 min in Tris-buffered saline and incubated in blocking buffer consisting of Tris-saline-5% BSA. The paper is then incubated with antiserum to peptides 1, 2, 3 and 4 above in Tris-saline-BSA-0.1% Triton X-100 for 2 hr, rinsed and immersed again in blocking buffer for 30 min. The paper is then incubated in 300,000 cpm of $^{125}$I-protein A in Tris-saline-BSA-Triton X-100 for 1 hr at 37° C., washed and dried. The squares are cut out and assayed for radioactivity in a gamma scintillation counter.

For biopsies, immunoperoxidase staining is most convenient. The avidin/biotin method described by Hsu, S. M., et al. *Advances in Immunohistochemistry* (1984) Medical Publishers, pp. 31–42 was used.

The tissue sections are immersed in 3% hydrogen peroxide to block endogenous peroxidase activity. The slides are then washed in distilled water and PBS, and then immersed in 3% normal goat serum.(Vector Laboratories) to block nonspecific binding. The peptide antisera are then added in dilutions ranging from 1:100 to 1:2000 and incubated overnight at 4° C. The slides are rinsed in PBS and incubated with goat anti-rabbit IgG, and then reacted with avidin/biotin complex (ABC) reagent (Vector Laboratories) for a minimum of 30 min. Labeling antibodies (ABC stain) is added for 30 min and the slides again rinsed in PBS. Chromogen reaction using diaminobenzedine (DAB) solution (0.05% Tris pH 7.6, DAB, 30% hydrogen peroxide) is then developed for 5 min, and the samples are rinsed, counterstained with hematoxylin and cover slipped. A positive staining is indicated by a black-brown chromogenic precipitate of DAB.

Figure 8A:
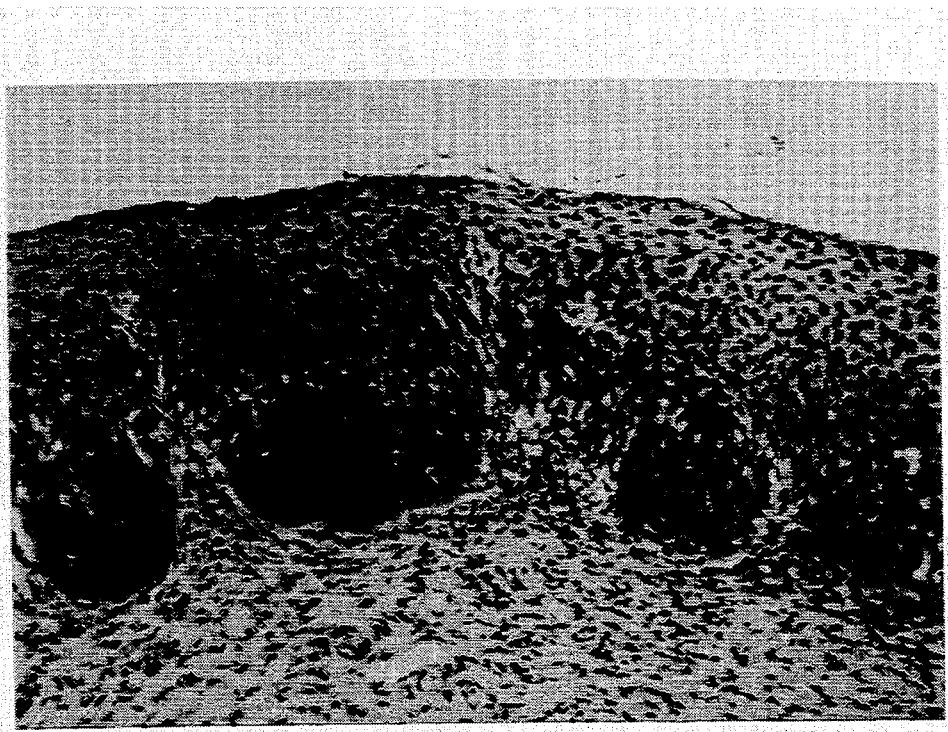
FIG. 8A shows the section stained with immune serum preabsorbed with the immunizing peptide.
Figure 8B:
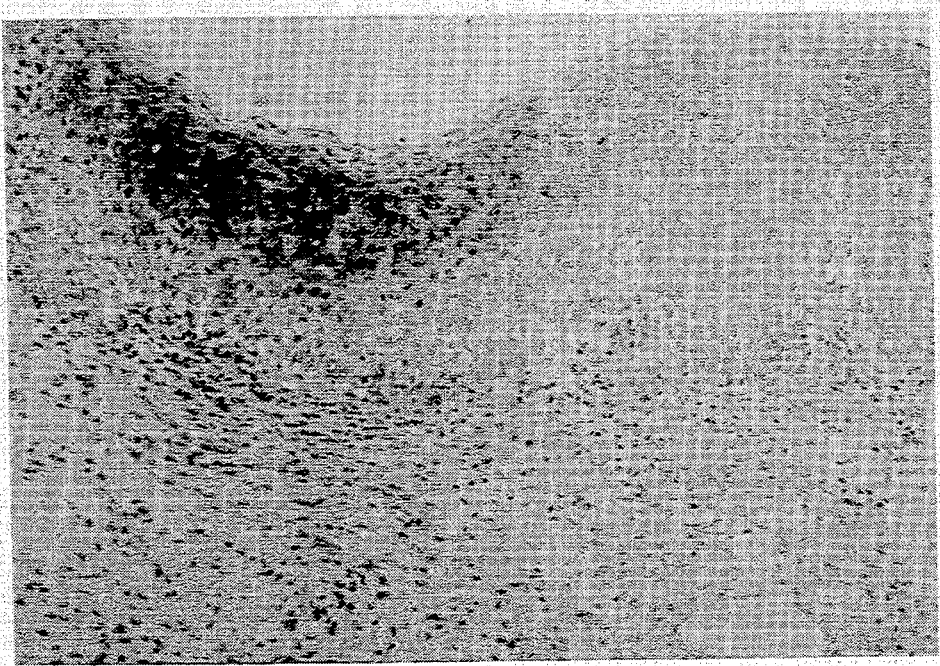
FIG. 8B shows the same section stained with the immune serum.
Figure 8C:
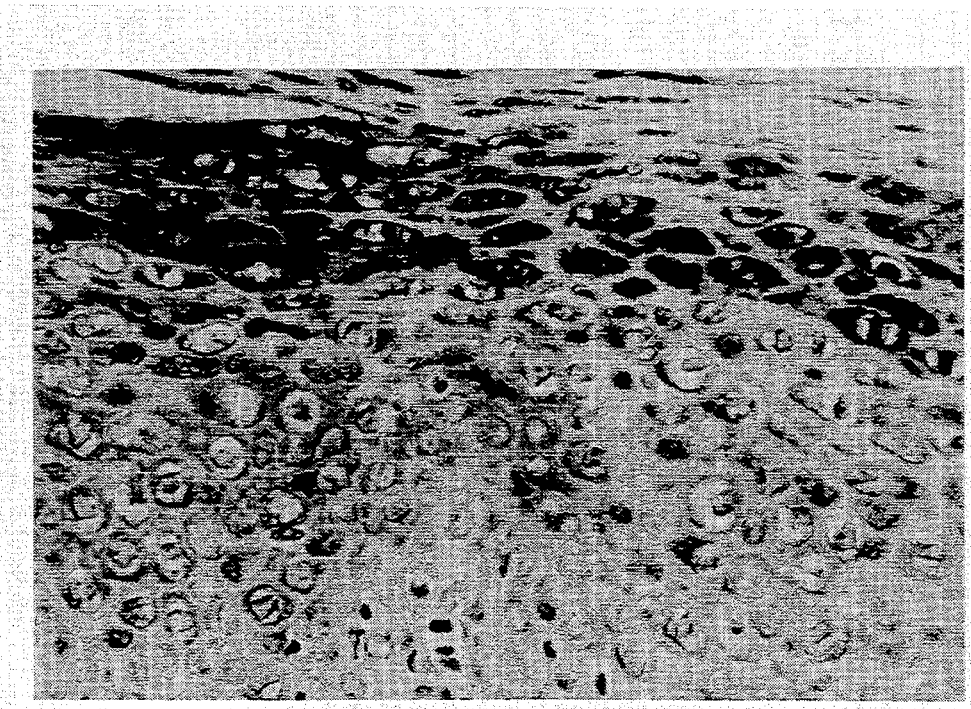
FIG. 8C shows a magnification of the stain in FIG. 8B.

FIG. 8 shows the results of staining of a single biopsy which is assessed as CIN 2 by pathology. FIG. 8A shows this section stained using rabbit antiserum prepared against peptide 1, but preadsorbed with the peptide by incubating the serum in the presence of excess peptide 1. As FIG. 8A shows, no DAB precipitate is detectable: the epithelial layer is clearly distinguishable from the stroma by apparent cell morphology with clear definition of the basement membrane. FIG. 8B is the same section stained using the same antisera, but unadsorbed with peptide 1. The epithelium clearly shows the presence of the CIN2 characteristics in this tissue. The HPV antigen is associated with this stage as demonstrated by the brown stain apparent in the photograph. The antigen does not appear in the stroma, since penetration of the basement membrane has not yet occurred in CIN2. FIG. 8C is a magnification of the stained area at the surface of the epithelium shown in FIG. 8B.

Figure 9:
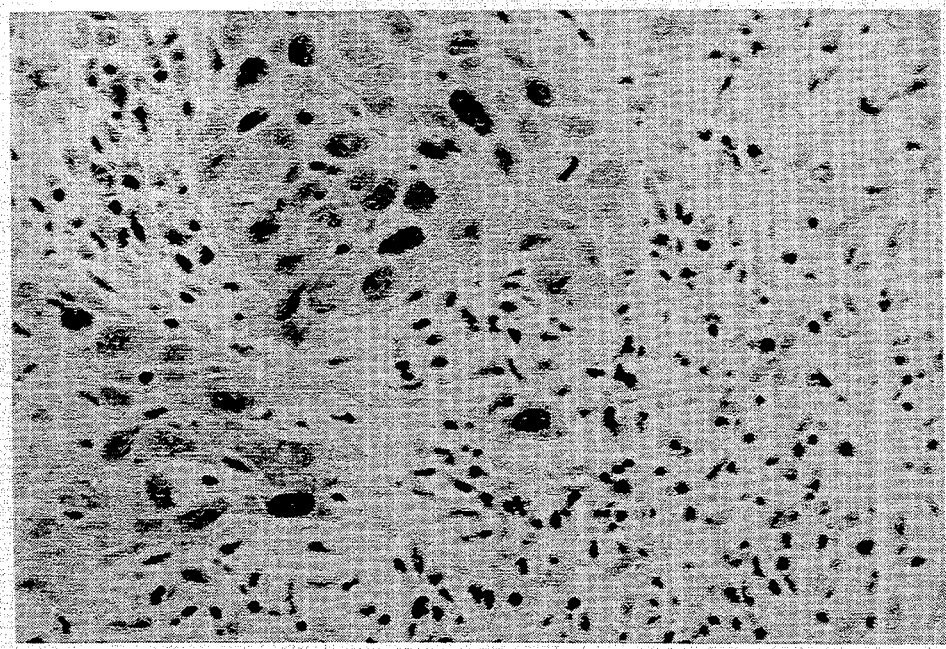
FIG. 9 shows the ability of the immunoperoxidase stain mediated by antibody of the invention to detect a single malignant cell.

FIG. 9 shows the ability of the immunoperoxidase method of the invention to detect the presence of a single malignant cell in the stroma. FIG. 9 is a magnified view of stained tissue from a patient where malignant transformation has already occurred and a pathologic diagnosis of cervical carcinoma has already been made. The cell at the center of the photograph is an isolated malignant cell exhibiting the HPV antigens.

The results illustrated in FIGS. 8 and 9 were obtained in the course of a study involving eleven patients as described above. In these assays, controls were run to show that no immunoreaction (brown stain) was ever observed using pre-immune serum or serum previously incubated with the immunizing peptide. These controls were run in all tests. Additional controls were also run with antisera to peptide 1, using samples known to contain HPV-16, HPV-18, HPV-6 or HPV-11. Only HPV-16 and 18 gave positive results and higher color intensity was obtained with HPV-16; this cross reactivity with HPV-18 shows that peptide 1 generates cross-type reacting antisera. Normal cervical swabs were also used as controls and no reaction was obtained using antisera obtained from any of the four peptides tested.

However, patients having known dysplasias did show positive results as set forth in Table 1 below. The results shown in Table 1 indicate that the test detects presence of the virus and tracks the progress of tissue differentiation caused by the stepwise expression of the vital genome.

TABLE 1

|  |  | Peptide # | | | |
| --- | --- | --- | --- | --- | --- |
|  |  | 1 | 2 | 3 | 4 |
| 2 patients CIN1 | HPV-16 DNA(−) | − | − | − | − |
| 6 patients CIN1 | HPV-16 DNA(+) | + | + | + | + |
| 4 patients CIN2 | HPV-16 DNA(+) | + | + | + | + |
| 2 patients CIN3 | HPV-16 DNA(+) | − | − | − | − |
| 1 patient SSC | HPV-16 DNA(+) | + | − | + | + |
| normal Adj CIN3 | HPV-16 DNA(+) | + | + | + | + |

The first two patients, listed in row 1 of Table 1, were assessed as having CIN1 stage lesions by pathology. However, the absence of HPV-16 virus in these patients (indicated by the (−)) was determined by Southern blot DNA hybridization performed on the smear. As shown, these patients also tested negative for the presence of HPV-16 using the antisera. On the other hand, the six patients also showing CIN1 by pathology, but shown to harbor HPV-16 by Southern blot DNA hybridization (labeled (+)), gave positive results with the antisera. The four patients assessed as CIN2 gave clear positive tests with the antisera for the presence of HPV.

However, two patients assessed as CIN3 were unreactive with all sera presumably because of the differentiation state of the tissue at this stage. The biopsy from one patient was assessed independently, but the other CIN3 tissue was obtained adjacent to one of the CIN2 samples in the preceding row. This confirms that the test with antiserum makes possible an objective differentiation between CIN2 and CIN3. This is sometimes difficult to ascertain by visual inspection; i.e. the findings of a single pathologist will generally be internally consistent, but there are frequently differences between the assessments given by different pathologists.

As shown in the next-to-bottom line of the table, a patient having a known carcinoma was positive with respect to peptides 1, 3 and 4 but negative with respect to peptide 2, presumably indicating alteration in genomic integration, transcription, or post-transcription events which may occur when the cells become malignant. The last line of the table gives the results for normal tissue obtained from a patient who also had CIN3 tissue which had tested negative against all antisera, but which CIN3 tissue had been shown to contain HPV-16 DNA by Southern blot. The positive results indicate that latent virus, and even gene expression products remain in the normal cells when adjacent tissues are in later stages of the infection.

We claim:
1. A method for indicating the presence of human papilloma virus in a clinical sample which comprises the steps of:
   (a) providing an antibody-containing composition, said composition containing antibody immunospecific for an epitope having an amino acid sequence selected from the group consisting of
      (1) Ser-Arg-Ser-Ser-Arg-Thr-Arg-Arg-Glu-Thr-Gln-Leu (SEQ ID NO:1) (representing residues 147–158 of E6 except Ser was substituted for Cys at position 1);
      (2) Phe-Gln-Asp-Pro-Gln-Glu-Arg-Pro-Arg-Lys-Leu-Pro-Gln-Leu-Cys (SEQ ID NO:2), representing residues 9–23 of E6;
      (3) Thr-Glu-Leu-Gln-Thr-Thr-Ile-His-Asp-Ile-Ile-Leu-Glu-Cys (SEQ ID NO:3), representing residues 24–37 of E6;
      (4) Leu-Arg-Arg-Glu-Val-Tyr-Asp-Phe-Ala-Phe-Arg-Asp-Leu-Cys (SEQ ID NO:4), representing residues 45–58 of E6;
      (5) Asp-Lys-Lys-Gln-Arg-Phe-His-Asn-Ile-Arg (SEQ ID NO:5), representing residues 127–136;
      (6) Gly-Pro-Ala-Gly-Gln-Ala-Glu-Pro-Asp-Arg-Ala (SEQ ID NO:6), representing residues 40–50 of E7;
      (7) Asp-Thr-Pro-Thr-Leu-His-Glu-Tyr-Met (SEQ ID NO:7), representing residues 4–12 of E7;
      (8) Asn-Asp-Ser-Ser-Glu-Glu-Glu-Asp-Glu-Ile-Asp-Gly (SEQ ID NO:8), representing residues 29–40 of E7;
      (9) Leu-Gln-Leu-Thr-Leu-Glu-Thr-Ile-Tyr-Asn-Ser (SEQ ID NO:9), representing residues 75–85 of E2;
      (10) Ile-Ile-Arg-Gln-His-Leu-Ala-Asn-His-Pro (SEQ ID NO:10), representing residues 210–219 of E2;
      (11) His-Pro-Ala-Ala-Thr-His-Thr-Lys-Ala-Val-Ala-Leu-Gly (SEQ ID NO:11), representing residues 218–230 of E2;
      (12) Ser-Glu-Trp-Gln-Arg-Asp-Gln-Phe-Leu-Ser-Gln-Val (SEQ ID NO:12), representing residues 339–350 of E2;
      (13) Asp-Gln-Asp-Gln-Ser-Gln-Thr-Pro-Glu-Thr-Pro (SEQ ID NO:13), representing residues 48–58 of E4;
      (14) Gly-Ser-Thr-Trp-Pro-Thr-Thr-Pro-Pro-Arg-Pro-Ile-Pro-Lys-Pro (SEQ ID NO:14), representing amino acids 20–34 of E4;
      (15) Arg-Leu-Tyr-Leu-His-Glu-Asp-Glu-Asp-Lys-Glu-Asn (SEQ ID NO:15), representing amino acids 476–487 of E1; and
      (16) Ala-Pro-Ile-Leu-Thr-Ala-Phe-Asn-Ser-Ser-His-Lys-Gly-Cys (SEQ ID NO:16), representing amino acids 218–230 of E2;
      wherein all the foregoing are derived from Type 16; and
      (17) Glu-Ser-Ala-Asn-Ala-Ser-Thr-Ser-Ala-Thr-Thr-Ile-Cys (SEQ ID NO:17), representing amino acids 6–17 of the E6 reading frame of Type 6B,
   (b) contacting said clinical sample with said composition under antibody-antigen complex formation conditions,
   (c) detecting the formation of antibody-antigen complex resulting from the contacting of step (b), and
   (d) relating the detection of complex of step (c) to the presence in the clinical sample of human papilloma virus.

2. A method for distinguishing CIN2 and CIN3 stages of human papilloma virus infection in a clinical sample selected from the group consisting of a cervical biopsy and a cervical smear which comprises the steps of:
   (a) providing an antibody-containing composition, said composition containing antibody immunospecific for an epitope having an amino acid sequence selected from the group consisting of
      (1) Ser-Arg-Ser-Ser-Arg-Thr-Arg-Arg-Glu-Thr-Gln-Leu (SEQ ID NO:1) (representing residues 147–158 of E6 except Ser was substituted for Cys at position 1);
      (2) Phe-Gln-Asp-Pro-Gln-Glu-Arg-Pro-Arg-Lys-Leu-Pro-Gln-Leu-Cys (SEQ ID NO:2), representing residues 9–23 of E6;
      (3) Thr-Glu-Leu-Gln-Thr-Thr-Ile-His-Asp-Ile-Ile-Leu-Glu-Cys (SEQ ID NO:3), representing residues 24–37 of E6;
      (4) Leu-Arg-Arg-Glu-Val-Tyr-Asp-Phe-Ala-Phe-Arg-Asp-Leu-Cys (SEQ ID NO:4), representing residues 45–58 of E6;
      (5) Asp-Lys-Lys-Gln-Arg-Phe-His-Asn-Ile-Arg (SEQ ID NO:5), representing residues 127–136;
      (6) Gly-Pro-Ala-Gly-Gln-Ala-Glu-Pro-Asp-Arg-Ala (SEQ ID NO:6), representing residues 40–50 of E7;
      (7) Asp-Thr-Pro-Thr-Leu-His-Glu-Tyr-Met (SEQ ID NO:7), representing residues 4–12 of E7;
      (8) Asn-Asp-Ser-Ser-Glu-Glu-Glu-Asp-Glu-Ile-Asp-Gly (SEQ ID NO:8), representing residues 29–40 of E7;
      (9) Leu-Gln-Leu-Thr-Leu-Glu-Thr-Ile-Tyr-Asn-Ser (SEQ ID NO:9), representing residues 75–85 of E2;
      (10) Ile-Ile-Arg-Gln-His-Leu-Ala-Asn-His-Pro (SEQ ID NO:10), representing residues 210–219 of E2;
      (11) His-Pro-Ala-Ala-Thr-His-Thr-Lys-Ala-Val-Ala-Leu-Gly (SEQ ID NO:11), representing residues 218–230 of E2;
      (12) Ser-Glu-Trp-Gln-Arg-Asp-Gln-Phe-Leu-Ser-Gln-Val (SEQ ID NO:12), representing residues 339–350 of E2;
      (13) Asp-Gln-Asp-Gln-Ser-Gln-Thr-Pro-Glu-Thr-Pro (SEQ ID NO:13), representing residues 48–58 of E4;
      (14) Gly-Ser-Thr-Trp-Pro-Thr-Thr-Pro-Pro-Arg-Pro-Ile-Pro-Lys-Pro (SEQ ID NO:14), representing amino acids 20–34 of E4;
      (15) Arg-Leu-Tyr-Leu-His-Glu-Asp-Glu-Asp-Lys-Glu-Asn (SEQ ID NO:15), representing amino acids 476–487 of E1; and

(16) Ala-Pro-Ile-Leu-Thr-Ala-Phe-Asn-Ser-Ser-His-Lys-Gly-Cys (SEQ ID NO:16), representing amino acids 218-230 of E2;
wherein all the foregoing are derived from Type 16; and
(17) Glu-Ser-Ala-Asn-Ala-Ser-Thr-Ser-Ala-Thr-Thr-Ile-Cys (SEQ ID NO:17), representing amino acids 6–17 of the E6 reading frame of Type 6B, (b) contacting said clinical sample with said composition under antibody-antigen complex formation conditions,
(c) detecting the formation of antibody-antigen complex resulting from the contacting of step (b), and
(d) relating the detection of complex of step (c) to the presence in the clinical sample of CIN3 stage human papilloma virus infection.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Ser Arg Ser Ser Arg Thr Arg Arg Glu Thr Gln Leu
1               5                   10
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Phe Gln Asp Pro Gln Glu Arg Pro Arg Lys Leu Pro Gln Leu Cys
1               5                   10                  15
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Thr Glu Leu Gln Thr Thr Ile His Asp Ile Ile Leu Glu Cys
1               5                   10
```

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Leu Arg Arg Glu Val Tyr Asp Phe Ala Phe Arg Asp Leu Cys
1               5                   10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Asp Lys Lys Gln Arg Phe His Asn Ile Arg
1               5                   10
```

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Gly  Pro  Ala  Gly  Gln  Ala  Glu  Pro  Asp  Arg  Ala
1                   5                        10
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Asp  Thr  Pro  Thr  Leu  His  Glu  Tyr  Met
1                   5
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
Asn  Asp  Ser  Ser  Glu  Glu  Glu  Asp  Glu  Ile  Asp  Gly
1                   5                        10
```

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Leu  Gln  Leu  Thr  Leu  Glu  Thr  Ile  Tyr  Asn  Ser
1                   5                        10
```

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

```
Ile  Ile  Arg  Gln  His  Leu  Ala  Asn  His  Pro
1                   5                        10
```

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

```
    His  Pro  Ala  Ala  Thr  His  Thr  Lys  Ala  Val  Ala  Leu  Gly
    1              5                   10
```

( 2 ) INFORMATION FOR SEQ ID NO:12:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( x i ) SEQUENCE DESCRIPTION: SEQ ID NO:12:

```
    Ser  Glu  Trp  Gln  Arg  Asp  Gln  Phe  Leu  Ser  Gln  Val
    1              5                   10
```

( 2 ) INFORMATION FOR SEQ ID NO:13:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( x i ) SEQUENCE DESCRIPTION: SEQ ID NO:13:

```
    Asp  Gln  Asp  Gln  Ser  Gln  Thr  Pro  Glu  Thr  Pro
    1              5                   10
```

( 2 ) INFORMATION FOR SEQ ID NO:14:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( x i ) SEQUENCE DESCRIPTION: SEQ ID NO:14:

```
    Gly  Ser  Thr  Trp  Pro  Thr  Thr  Pro  Pro  Arg  Pro  Ile  Pro  Lys  Pro
    1              5                   10                            15
```

( 2 ) INFORMATION FOR SEQ ID NO:15:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( x i ) SEQUENCE DESCRIPTION: SEQ ID NO:15:

```
    Arg  Leu  Tyr  Leu  His  Glu  Asp  Glu  Asp  Lys  Glu  Asn
    1              5                   10
```

( 2 ) INFORMATION FOR SEQ ID NO:16:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( x i ) SEQUENCE DESCRIPTION: SEQ ID NO:16:

```
    Ala  Pro  Ile  Leu  Thr  Ala  Phe  Asn  Ser  Ser  His  Lys  Gly  Cys
    1              5                   10
```

( 2 ) INFORMATION FOR SEQ ID NO:17:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( x i ) SEQUENCE DESCRIPTION: SEQ ID NO:17:

```
Glu Ser Ala Asn Ala Ser Thr Ser Ala Thr Thr Ile Cys
 1           5                   10
```